United States Patent
Mischi et al.

(10) Patent No.: US 11,284,864 B2
(45) Date of Patent: Mar. 29, 2022

(54) SHEAR WAVE VISCOELASTICITY IMAGING USING LOCAL SYSTEM IDENTIFICATION

(71) Applicant: Technische Universiteit Eindhoven, Eindhoven (NL)

(72) Inventors: Massimo Mischi, Eindhoven (NL); Ruud Johannes Gerardus Van Sloun, Eindhoven (NL)

(73) Assignee: TECHNISCHE UNIVERSITES EINDHOVEN, Eindhoven (NL)

( * ) Notice: Subject to any disclaimer, the term of this patent is extended or adjusted under 35 U.S.C. 154(b) by 63 days.

(21) Appl. No.: 16/620,216

(22) PCT Filed: Jun. 7, 2018

(86) PCT No.: PCT/EP2018/065054
§ 371 (c)(1),
(2) Date: Dec. 6, 2019

(87) PCT Pub. No.: WO2018/224602
PCT Pub. Date: Dec. 13, 2018

(65) Prior Publication Data
US 2020/0121288 A1   Apr. 23, 2020

(30) Foreign Application Priority Data
Jun. 9, 2017   (EP) .................................... 17175173

(51) Int. Cl.
*A61B 8/08*   (2006.01)
*A61B 8/00*   (2006.01)
(Continued)

(52) U.S. Cl.
CPC ............ *A61B 8/485* (2013.01); *A61B 8/5207* (2013.01); *A61B 8/587* (2013.01); *G01N 29/032* (2013.01);
(Continued)

(58) Field of Classification Search
CPC ....... A61B 8/485; A61B 8/5207; A61B 8/587; G01N 29/032; G01N 29/0645;
(Continued)

(56) References Cited

U.S. PATENT DOCUMENTS

| 8,394,026 B2* | 3/2013 | Eskandari .............. A61B 8/587 |
| | | 600/438 |
| 8,469,891 B2* | 6/2013 | Maleke ................ A61B 8/5261 |
| | | 600/438 |

(Continued)

FOREIGN PATENT DOCUMENTS

| EP | 1065492 A2 | 1/2001 |
| WO | WO2014/201020 A1 | 12/2014 |

OTHER PUBLICATIONS

International Search Report and Written Opinion for PCT Patent App. No. PCT/EP2018/065054 (dated Aug. 14, 2018).

(Continued)

*Primary Examiner* — Octavia Hollington
(74) *Attorney, Agent, or Firm* — Kenealy Vaidya LLP

(57) ABSTRACT

Some embodiments relate to a system and method of estimating the viscoelasticity of a material. The system and method includes
receiving a plurality of time-amplitude curves measured at a plurality of space points. The time-amplitude curves reflect time evolutions of a propagating mechanical wave.
The system and method also include estimating the viscoelasticity of a material between any set of space points using the time-amplitude curves measured at those space points.

11 Claims, 10 Drawing Sheets

(51) Int. Cl.
G01N 29/032 (2006.01)
G01N 29/06 (2006.01)
G01N 29/11 (2006.01)
G01N 29/44 (2006.01)
G01S 7/52 (2006.01)
G01S 15/89 (2006.01)

(52) U.S. Cl.
CPC ......... G01N 29/0645 (2013.01); G01N 29/11 (2013.01); G01N 29/4472 (2013.01); G01S 7/52042 (2013.01); G01S 15/8918 (2013.01); G01N 2203/0094 (2013.01); G01N 2291/02818 (2013.01); G01N 2291/02827 (2013.01)

(58) Field of Classification Search
CPC ............... G01N 29/11; G01N 29/4472; G01N 2203/0094; G01N 2291/02818; G01N 2291/02827; G01S 7/52042; G01S 15/8918
USPC .......................................................... 73/789
See application file for complete search history.

(56) References Cited

U.S. PATENT DOCUMENTS

| | | | |
|---|---|---|---|
| 10,420,528 B2* | 9/2019 | Zhai | A61B 8/08 |
| 11,002,712 B2* | 5/2021 | Walker | G01N 29/4418 |
| 2010/0138163 A1 | 6/2010 | Gallippi et al. | |
| 2013/0174666 A1* | 7/2013 | Hadj Henni | G01L 1/24 73/800 |
| 2016/0274015 A1* | 9/2016 | Hadj Henni | G01N 3/34 |

OTHER PUBLICATIONS

Van Sloun, R., et al., "Ultrasound Coefficient of Nonlinearity Imaging," IEEE Transactions on Ultrasonics, Ferroelectrics, and Frequency Control 2015;62(7):1331-1341.
J McLaughlin, et al., "Shear wave speed recovery in transient elastography and supersonic imaging using propagating fronts," Institute of Physics Publishing, Inverse Problems 22 (2006) 681-706.
T Loupas, et al., "An Axial Velocity Estimator for Ultrasound Blood Flow Imaging, Based on a Full Evaluation of the Doppler Equation by Means of a Two-Dimensional Autocorrelation Approach," IEEE Transactions on Ultrasonics, Ferroelectrics, and Frequency Control, vol. 42, No. 4, Jul. 1995, pp. 672-688.
N Rouze, et al., "Robust Estimation of Time-of-Flight Shear Wave Speed Using a Radon Sum Transformation," IEEE Trans Ultrason Ferroelectr Freq Control. Dec. 2010 ; 57(12): 2662-2670.

K Hoyt, et al., "Tissue elasticity properties as biomarkers for prostate cancer," Cancer Biomark. 2008 ; 4(4-5): 23 pages.
M Palmeri, et al., "Quantifying Hepatic Shear Modulus In Vivo Using Acoustic Radiation Force," Ultrasound Med Biol. Apr. 2008; 34(4): 26 pages.
M Wang, et al., "In-Vivo Quantification of Liver Stiffness in a Rat Model of Hepatic Fibrosis with Acoustic Radiation Force," Ultrasound Med Biol. Oct. 2009 ; 35(10): 25 pages.
M Wang, et al., "Improving the Robustness of Time-of-Flight Based Shear Wave Speed Reconstruction Methods Using RANSAC in Human Liver in vivo," Ultrasound Med Biol. May 2010 ; 36(5): 23 pages.
M Insana et al., "Viscoelastic Imaging of Breast Tumor Microenvironment With Ultrasound," J Mammary Gland Biol Neoplasia. Oct. 2004 ; 9(4): 18 pages.
R E Kalman, "A New Approach to Linear Filtering and Prediction Problems," Transactions of the ASME—Journal of Basic Engineering, 82 (Series D) 1960: 35-45.
R Righetti et al., "The feasibility of estimating and imaging the mechanical behavior of poroelastic materials using axial strain elastography," IOP Publishing, Phys. Med. Biol. 52 (2007) 3241-3259.
M Sridhar et al., "Ultrasonic measurements of breast viscoelasticity," Med Phys. Dec. 2007 ; 34(12): 22 pages.
T Stamey et al., "Localized Prostate Cancer Relationship of Tumor Volume to Clinical Significance for Treatment of Prostate Cancer," CANCER Supplement Feb. 1, 1993, vol. 71, No. 3, 933-938.
N Rouze et al., "An analytic, Fourier domain description of shear wave propagation in a viscoelastic medium using asymmetric Gaussian sources," J. Acoust. Soc. Am. 138 (2), Aug. 2015, 1012-1022.
T Deffieux et al., "Investigating liver stiffness and viscosity for fibrosis, steatosis and activity staging using shear wave elastography," Journal of Hepatology, vol. 62, Issue 2, p. 317-324, Feb. 1, 2015.
Y Wang et al., "Ultrasonic Imaging—Viscoelastic Properties of Rodent Mammary Tumors Using Ultrasonic Shear-Wave Imaging," First Published Mar. 14, 2013, https://journals.sagepub.com/doi/10.1177/0161734613477321, 8 pages.
J Bercoff et al., "The Role of Viscosity in the Impulse Diffraction Field of Elastic Waves Induced the Acoustic Radiation Force," IEEE Transactions on Ultrasonics, Ferroelectrics, and Frequency Control, vol. 51, No. 11, Nov. 2004, 13 pages.
I Nenadic et al., "Model-free quantification of shear wave velocity and attenuation in tissues and its in vivo application," The Journal of the Acoustical Society of America: vol. 134, No. 5, 2013, 4 pages.
J Bercoff, et al., "Supersonic shear imaging: a new technique for soft tissue elasticity mapping," IEEE Transactions on Ultrasonics, Ferroelectrics, and Frequency Control, Apr. 1, 2004, 51(4): 2 pages.
K Nightingale, et al., "Shear-wave generation using acoustic radiation force: in vivo and ex vivo results," ScienceDirect, Ultrasound in Medicine & Biology vol. 29, Issue 12, Dec. 2003, 3 pages.

* cited by examiner

Fig. 1A
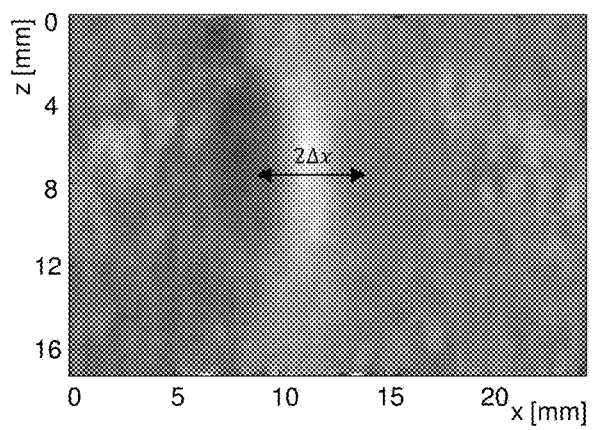
Fig. 1B
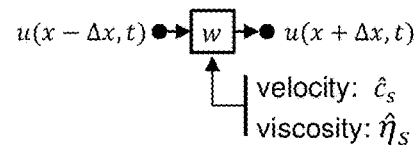
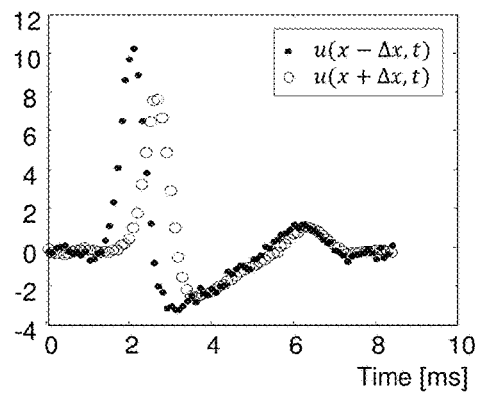
Fig. 1C
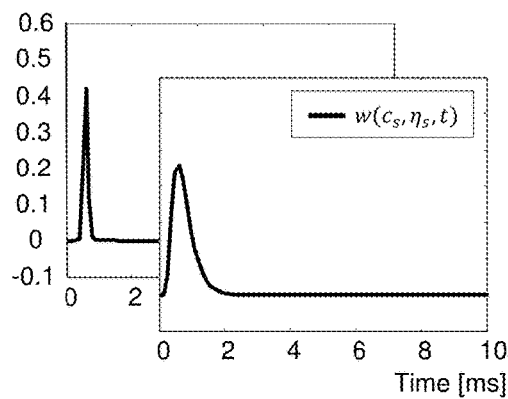
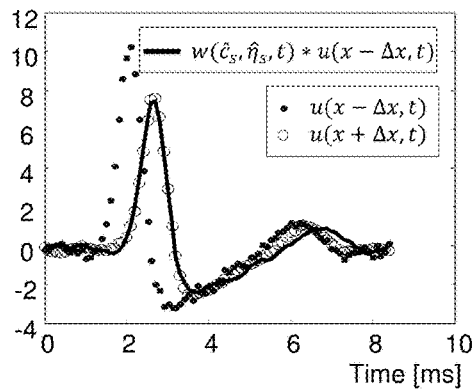
Fig. 1D  Fig. 1E Fig. 6B  SW velocity Fig. 6D  SW velocity

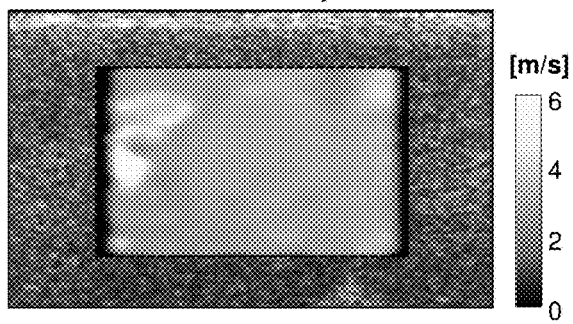
Fig. 6E  SW velocity
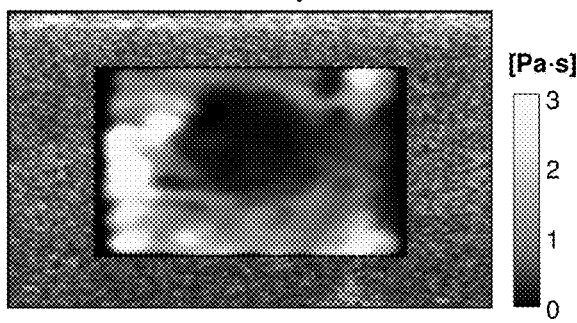
Fig. 6F  Viscosity
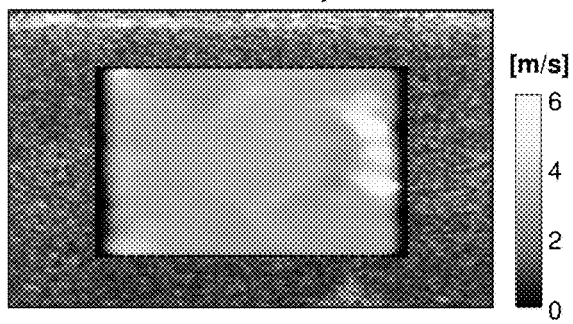
Fig. 6G  SW velocity
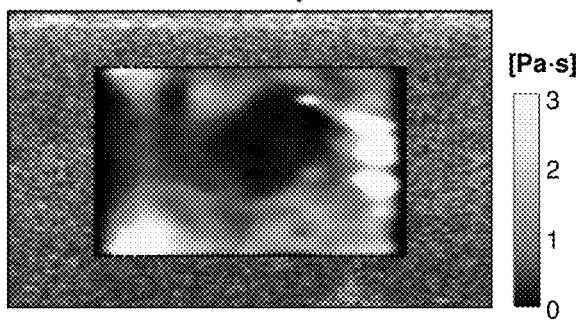
Fig. 6H  Viscosity

SHEAR WAVE VISCOELASTICITY IMAGING USING LOCAL SYSTEM IDENTIFICATION

CROSS REFERENCE TO RELATED APPLICATIONS

This application is a national phase filing under 35 C.F.R. § 371 of and claims priority to PCT Patent Application No. PCT/EP2018/065054, filed on Jun. 7, 2018, which claims the priority benefit under 35 U.S.C. § 119 of European Patent Application No. 17175173.8, filed on Jun. 9, 2017, the contents of each of which are hereby incorporated in their entireties by reference.

BACKGROUND

The presently disclosed subject matter relates to a system and a method of estimating the viscoelasticity of a material. The presently disclosed subject matter particularly relates to estimating the viscoelasticity of tissue. The presently disclosed subject matter also relates to a method of detecting abnormalities in living tissue.

Imaging technologies that allow assessment of the elastic properties of soft tissue provide clinicians with an asset for several diagnostic applications. Pathologies such as tissue fibrosis and cancer are linked to tissue elasticity, and accurate detection and staging of these pathologies is fundamental for providing adequate treatment and disease management.

For this purpose, manual palpation is used extensively in clinical routine. Among the elastographic possibilities, there is a particular ultrasound-based solution that enables remote palpation using acoustic radiation force: shear wave (SW) elasticity imaging. By applying a push-pulse using high intensity focused ultrasound, tissue is locally displaced in the axial direction, causing the formation of a laterally propagating SW. If one considers the medium to be purely elastic, its local shear modulus can be estimated by determining the local SW speed. In practice, this assumption does however not hold for many tissue types; tissue in which not only the stiffness, but also the shear viscosity plays a role. Moreover, there is increasing evidence for the idea that viscosity itself could be a discriminant parameter for malignancy detection.

In [1], Hoyt et al. assessed the elastic properties of prostate cancer tissue for their relevance as biomarkers. Their results revealed that the viscosity of cancerous prostate tissue is greater than that derived from normal tissue. In the presently disclosed subject matter described below, we therefore aim at providing a joint estimate of tissue elasticity and viscosity based on SW elastography. Initially, inversion of the Helmholz equation was used to reconstruct SW speed from time-displacement data [2], [3]. However, calculating the second-order derivatives in space and time makes such an estimator very susceptible to the noisy signal conditions one can expect in-vivo. More recently developed methods assess SW speed by calculating the wave arrival time across a set of axial displacement curves.

In [4], [5], SW speed was obtained by assessing the lateral time-to-peak and exploiting linear regression to determine the rate-of-change across the set. Later, a more robust version of this approach was developed [6], in which a random sample consensus (RANSAC) algorithm was employed to reliably perform such a regression in the presence of strong outliers. In, [7], Rouze et al. showed that the SW time-of-flight can also be estimated using a Radon sum transformation, yielding a comparable robustness with respect to the RANSAC algorithm. An alternative approach determined the local SW speed by cross-correlating the displacement waveform at a specific position with that obtained at a reference location [8].

All of the above methods operate under the explicit assumption of negligible viscous dispersion across the evaluated region. To assess the SW dispersion that originates from viscosity, Nenadic et al. [9] devised a method that relates the two-dimensional Fourier transform of time-displacement data to the frequency dependent shear wave phase velocity. By calculating the wave number (spatial frequency) that maximizes the spectrum at a given temporal frequency the phase velocity at each frequency can be obtained, which in turn can be parametrized using typical viscoelastic material models such as the Voigt model. However, obtaining sufficient spatial frequency resolution to perform an accurate and reliable phase velocity estimate may require the use of a relatively large amount of space points.

SUMMARY

It is an aspect of the presently disclosed subject matter to improve the estimation of elasticity in a material such as in tissue.

A first aspect of the presently disclosed subject matter provides a method of estimating the viscoelasticity of a material, the method including:
receiving a plurality of time-amplitude curves measured at a plurality of space points, wherein the time-amplitude curves reflect time evolutions of a propagating mechanical wave;
estimating the viscoelasticity of a material between any set of space points using the time-amplitude curves measured at those space points.

Embodiments are defined in the dependent claims.

A method in accordance with the first aspect of the presently disclosed subject matter provides for a joint estimation of both elasticity and viscosity in the material. By doing this joint estimation the accuracy of the elasticity estimates will be improved, which normally are based on the assumption of negligible viscosity.

The presently disclosed subject matter also relates to a system for estimating the viscoelasticity of a material, the system including:
a receiver for receiving a plurality of time-amplitude curves measured at a plurality of space points, wherein the time-amplitude curves reflect time evolutions of a propagating mechanical wave;
an estimator for estimating the viscoelasticity of a material between any set of space points using the time-amplitude curves measured at those space points.

The presently disclosed subject matter also relates to a method of detecting abnormalities in living tissue, the method including:
radiating at least part of the living tissue using ultrasound waves;
detecting echoes of the ultrasound waves;
estimating the viscoelasticity of the living tissue using the method as described above.

BRIEF DESCRIPTION OF THE FIGURES

These and other aspects of the presently disclosed subject matter are apparent from and will be elucidated with reference to the embodiments described hereinafter. In the drawings:

FIGS. 1A, 1B, 1C, 1D, 1E show an illustrative overview of the proposed method, showing how the point-to-point impulse response is estimated from the time displacement curves sampled at two spatial locations x−Δx and x+Δx;

FIGS. 6B and 6D show standard elastographic velocity estimation results obtained using a time-of-flight method;

FIG. 6E-6H show pictures of the proposed shear wave viscoelasticity imaging method, yielding both velocity and viscosity. The results obtained with the acoustic push focus positioned on the right lateral side (see FIGS. 6A, 6B, 6E, 6F) are compared to those obtained with a push on the other side (see FIGS. 6C, 6D, 6G, 6H);

Figure 2A:
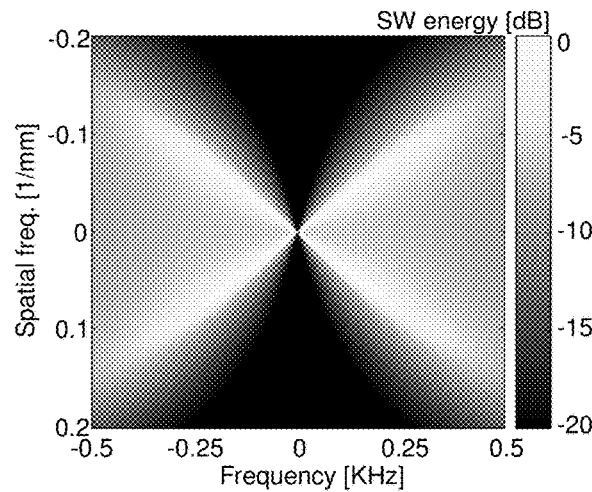
In FIG. 2A, the generated 2D Fourier domain SW data is shown and FIG. 2B gives the resulting particle velocity in the space-time domain.
Figure 2B:
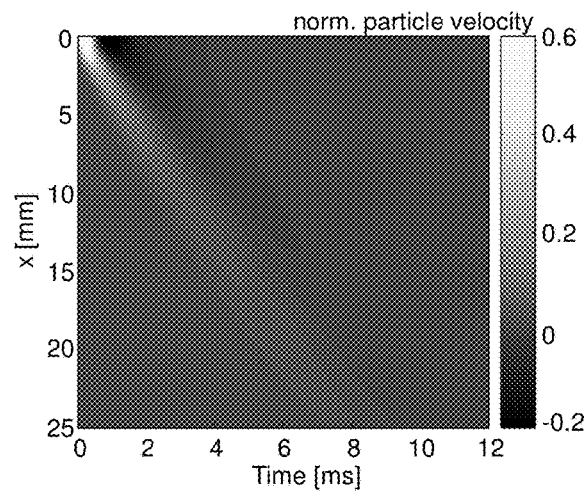
FIG. 2: Simulation of shear wave (SW) propagation in a viscoelastic material with $\mu_0$=9 kPa, $\rho$=1000 kg/m3, and $\eta_s$=1:5 Pa_s based on [12].
In FIG. 2C, several particle velocity signals at different lateral positions are shown as a function of time. Then, in FIG. 2D, the resulting SW velocity and viscosity estimates along the lateral position are summarized in box-plots. True values are indicated with dotted lines. For comparison, the results for SW velocity estimation based on a cross-correlation approach are also shown.
Figure 2C:
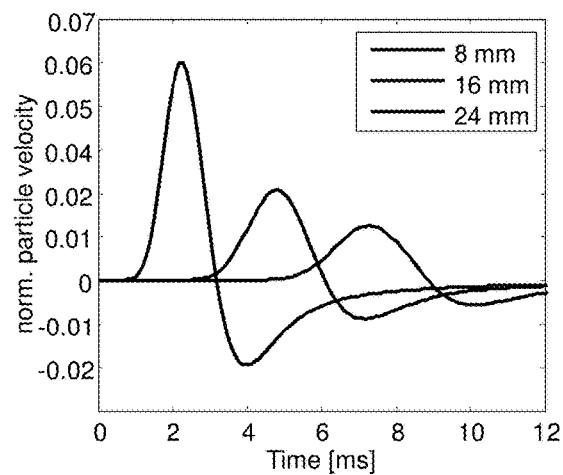
Figure 2D:
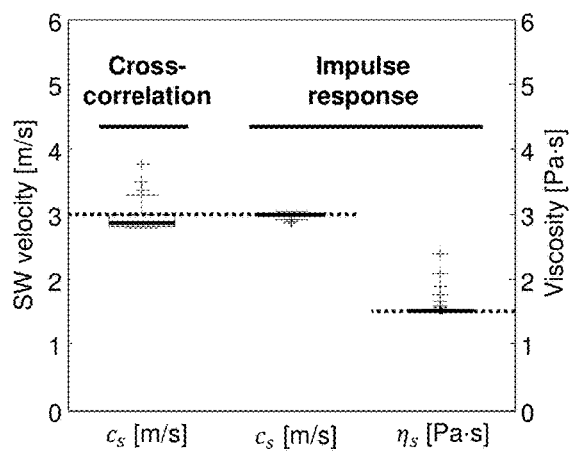

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EXEMPLARY EMBODIMENTS

In this presently disclosed subject matter, we consider the viscoelastic material as a dynamic linear system, of which the impulse response can be locally identified by input-output (point-to-point) analysis of SW time-displacement curves. To this end, a local model based estimator of the impulse response is derived from the Navier-Stokes equation, which is then fitted to the data in a least-squares fashion.

The SW data acquisition protocol and pre-processing steps are given in Sections II-A and II-B, respectively. Then, the details of the adopted signal model and an analytical description of the impulse response in viscoelastic materials are given (Sec. II-C). The impulse response is then estimated from the data to facilitate assessment of the aforementioned viscoelastic material-model parameters, as depicted in Section II-D. The method is then validated using simulated SW measurements (Sec. III-A) and in-vitro datasets (Sec. III-B), of which the results are presented in Section IV. Finally, in Section. V, these results are discussed and conclusions derived.

II. Methods

A. Data Acquisition

The experiments were performed using a Verasonics ultrasound research platform (Redmond, Wash., USA) in combination with an L11-4 linear array transducer. Shear waves (SW) were generated with acoustic radiation force, where the mechanical impulse delivered to the tissue is given by the product of acoustical force density and duration. Hence, to facilitate sufficient medium displacement, a 1500-cycle push-pulse with a center frequency of 4.5 MHz was adopted (excitation duration: 333 μs), and the excitation voltage was set to the maximum (overheating protected) value of 65 V. The resulting SW was tracked using an ultrafast imaging protocol operating at a frame rate of 10 kHz. A single-cycle pulse with a center frequency of 6.25 MHz was used. The in-phase & quadrature (IQ) data were reconstructed after dynamic receive beamforming of the radiofrequency (RF) data, and stored for off-line processing. The final pixel dimensions in the axial and lateral directions were 0:086 mm and 0:208 mm, respectively.

B. Pre-Processing

To reveal the laterally propagating SW, we estimate its micron scale axial displacements based on the well-known Loupass 2-D autocorrelator [10]. Initially developed for measuring blood flow velocity in Doppler systems, this approach estimates the mean axial velocity at each location by evaluating the 2D autocorrelation function of the IQ samples within a specific axial range and frame/ensemble range. In our experiments, these values were set to $N_{ax}$=20 samples (1.7 mm) and $N_{ens}$=5 frames (500 μs), respectively. Finally, the axial velocity maps were spatially filtered using a 2D Gaussian kernel with a standard deviation of 1.2 samples in both the axial and lateral direction.

C. Shear Wave Signal Model

For the purpose of estimating the SW propagation dynamics, we consider the displacement profiles measured at two laterally spaced pixels, see also FIG. 1A, and describe their relation as $$u(x+\Delta x,t)=w(\Delta x,t)*_t u(x-\Delta x,t) \quad (1)$$

wherein w(Δx,t) is the impulse response that characterizes the system describing the transition from u(x−Δx,t) to u(x+Δx,t). If one considers the SW propagation process as purely convective, the impulse response is a delayed delta function, and can be written as $$w(\Delta x,t)=\delta(t-2\Delta x/c_s) \quad (2)$$

with $c_s$ being the SW velocity. In this case, the model w(Δx,t) can be identified by simply maximizing the cross correlation function between the two displacement profiles in order to find their time-delay, and thereby the SW velocity. In viscoelastic media, shear waves do not merely propagate in a convective manner; their shape also spreads over space. The Navier-Stokes equation provides us with a more general framework. Adopting the classical Voigt model to describe the viscoelastic properties of tissue, SW particle displacements can be written as follows [11]:

$$\rho \partial_t^2 u(r,t) - (\rho c_s^2 + \eta_s \partial_t) \nabla^2 u(r,t) = S(r,t) \quad (3)$$

wherein $\eta_s$ is the viscosity, $\rho$ is the mass density and $S(r,t)$ is the excitation source. The spatiotemporal impulse response of this system, termed the Green's function $g(r, t)$, is then obtained by solving $$\rho \partial_t^2 g(r,t) - (\rho c_s^2 + \eta_s \partial_t) \nabla^2 g(r,t) = \delta(r)\delta(t) \quad (4)$$

In one space dimension, Eqn. (4) can be written in the 2D Fourier domain as:

$$-\rho \omega^2 G(k,\omega) + (\rho c_s^2 + j\omega \eta_s) k^2 G(k,\omega) = 1 \quad (5)$$

Equation (5) is derived specifically for a Voigt material. It can however easily be generalized to describe other material models in terms of a frequency dependent shear modulus $\mu(\omega)$ such that we obtain $$-\rho \omega^2 G(k,\omega) + \mu(\omega) k^2 G(k,\omega) = 1 \quad (6)$$

from which we can straightforwardly derive the following Green's function solution:

$$G(k,\omega) = (1/\rho)/[k^2 \mu(\omega)/\rho - \omega^2] \quad (7)$$

The inverse Fourier transform of (7) with respect to k is given by $$G(x, \omega) = \frac{\sqrt{\frac{\pi}{2}}}{j\omega \sqrt{\mu\left(\frac{\omega}{\rho}\right)}} \exp\left[-\frac{j\omega |x|}{\sqrt{\frac{\mu(\omega)}{\rho}}}\right] \quad (8)$$

From (8), the impulse response $w(\Delta x; t)$ from one space point to another can be described in the frequency domain as $$W(\Delta x, \omega) = \frac{G(|x| + 2\Delta x, \omega)}{G(|x|, \omega)} = \exp\left[-\frac{j\omega |2\Delta x|}{\sqrt{\frac{\mu(\omega)}{\rho}}}\right] \quad (9)$$

D. Shear Wave System Identification

To locally estimate the viscoelastic model parameters in the Voigt model ($\mu(\omega) = \rho c_s^2 + j\omega \eta_s$), from (1) and (9), we formulate the following nonlinear least squares problem:

$$\{\hat{c}_s, \hat{\eta}_s, \hat{\alpha}\}(x) = \min_{c_s \eta_s \alpha} |F^{-1}[W(\Delta x, \omega) U(x - \Delta x, \omega)] - u(x + \Delta x, t)|_2^2 \quad (10)$$

wherein $U(x-\Delta x, \omega)$ is the temporal Fourier transform of $u(x-\Delta x, t)$. This Fourier domain implementation of the convolution between $u(x-\Delta x, t)$ and $w(\Delta x, t)$ avoids aliasing that can occur when sampling the impulse response $w(\Delta x, t)$ in the time domain instead of the frequency domain, and allows for a computationally efficient implementation via the fast Fourier transform. Equation (10) is numerically solved in an iterative fashion using a Nelder-Mead simplex algorithm.

FIGS. 1A-1E gives an illustrative overview of the proposed method. FIG. 1B schematically shows the system to be identified, w. FIG. 1C shows two time-displacement curves at lateral positions $x-\Delta x$ and $x+\Delta x$. FIG. 1D illustrates the model-fitting procedure, which aims at identifying the model that fits the data (minimum mean squared error). An example of such a model fit to the data is given in FIG. 1E.

III. Validation Methodology

A. Simulation Study

The proposed method was first tested on simulated datasets by generating particle velocity measurements based on an analytic description of SW propagation in a viscoelastic medium following a Gaussian excitation as described in [12]. The cylindrically symmetric Gaussian excitation has the following form:

$$f(r, t) = W(t) \exp\left(-\frac{r^2}{\sigma^2}\right) \hat{z} \quad (11)$$

wherein $\hat{z}$ is the unit vector in the axial direction, $\sigma = 1$ mm gives the width and $W(t)$ determines the time profile of the excitation; a rectangular window with a length of $T = 333$ μs.

We adopted a Voigt material model, with stiffness $\mu_0$ and viscosity $\eta_s$, and generated 9 realizations of SW particle velocity measurements in materials with different degrees of viscosity. The datasets were then processed as described in Sections II-A to II-D in order to obtain estimates of SW velocity and viscosity as a function of the lateral position x. $\Delta x$ was set to 1.25 mm. The results are compared to those obtained using a standard cross-correlation based time-of-flight method for SW velocity estimation [8], and a two-dimensional Fourier transform (2D-FT) approach for frequency dependent SW phase velocity measurements [9]. The latter first calculates the 2D-FT of the full spatiotemporal SW signal, after which the average phase velocity at a specific temporal frequency is retrieved by locating the spatial frequency at which the 2D-FT is maximized: $c(f) = f = k_{max}(f)$.

B. In-Vitro Study

1) Phantom design: In our experiments, commercially available tofu (Unicurd Food Company Pte Ltd., Singapore) served as a typical high-viscosity material. Because its elastographic and echographic properties are similar to those of some soft tissues, this poroelastic soy-based product has been used as a viscous tissue-mimicking phantom [13]. To mimic low-viscosity tissues, water-based 8 weight-% gelatine was prepared [14], [15]. It included of 20-g gelatine, 9.95-g graphite scattering powder and 225-mL water. In total, we prepared 3 phantoms from these materials: two homogeneous phantoms (one tofu, one gelatine), and one tofu phantom with a cylindrical gelatine inclusion (diameter of 9 mm).

2) SW experiments: The SW experiments were performed as described in Section II-A. The data was then processed according to Sections II-A to II-D, with $\Delta x$ set to 1.25 mm.

3) Mechanical characterization: A material's viscoelastic behaviour is most straightforwardly revealed by assessing its creep curve, i.e., the time-dependent strain behaviour upon application of a constant load [13]. The instantaneous response to the compression is considered to be purely elastic, whereas the subsequent creep curve is attributed to viscosity [14]. The tofu and gelatine phantoms were cut into blocks of similar size (6 cm×5 cm×2 cm) and subjected to a pre-compression force of about 0.35 N. Then, their axial strain was monitored after the application of a sudden compressive load of about 200 g (2 N). For strain imaging during compression, ultrasound images were acquired at a frame rate of 50 Hz. Large frame-to-frame velocities (>1 sample/frame) were estimated by block-wise cross correlation of log-compressed B-mode frames (speckle tracking), and fine sub-sample displacements were captured by estimating the axial velocity from the IQ data using the Loupass 2-D autocorrelator [10]. The ensemble and axial ranges were set to 5 frames and 30 samples, respectively. The axial frame-to-frame displacements were then tracked over time using a Kalman filter [16] to measure the relative strain at a set depth after velocity estimation.

IV. Results

A. Simulation Results

FIG. 2 displays an example of a simulated dataset based on [12]. SW velocities $c_s$ and material viscosities $\eta_s$ are estimated along the lateral direction x based on the proposed method, and their distributions are summarized in box-plots (FIG. 2D). One can observe that the estimates are very close to the true values ($c_s$=3 m/s, $\eta_s$=1.5 kPa). Moreover, the SW velocity estimates seem to be slightly improved with respect to those obtained using the correlation-based time-of-flight approach [8].

Figure 3:
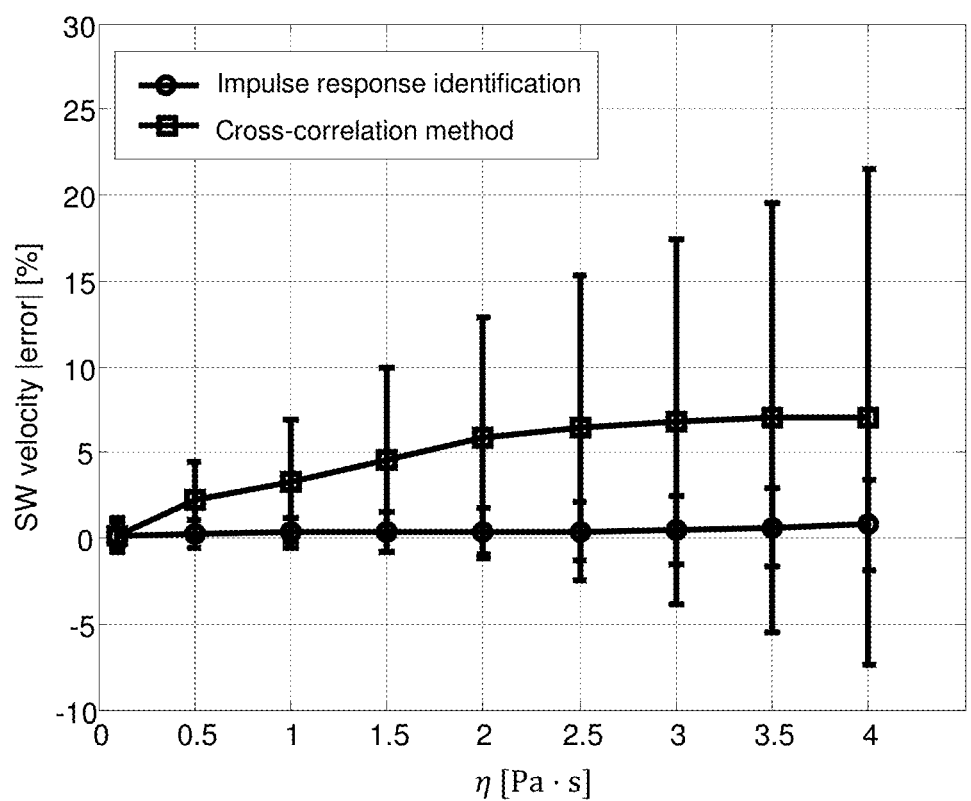
FIG. 3 shows a graph of shear wave velocity estimation errors in viscoelastic material simulations as a function of increasing viscosity. Bars in FIG. 3 indicate standard deviation of estimates across the lateral position. The proposed method is compared to a correlation-based time-of-flight method.

That considering viscosity in the estimation procedure leads to improved estimates of SW velocity in simulated data can also be noted from FIG. 3. The estimates of SW velocity based on the proposed impulse response identification procedure yielded lower errors and standard deviations compared to those obtained in a time-of-flight fashion, in particular for high viscosity.

In FIG. 4, we show how various levels of viscosity result in SW phase-velocity dispersion. To this end, the frequency dependent phase velocities were computed from the median estimates of $\eta_s$ and $c_s$ along the lateral direction x in the following manner [12]:

$$c(\omega) = \sqrt{\frac{2(\mu_0^2 + (\eta_s\omega)^2)}{\rho\left(\mu_0 + \sqrt{(\mu_0^2 + (\eta_s\omega)^2)}\right)}}$$

wherein the stiffness $\mu_0 = \rho c_s^2$.

Figure 4A:
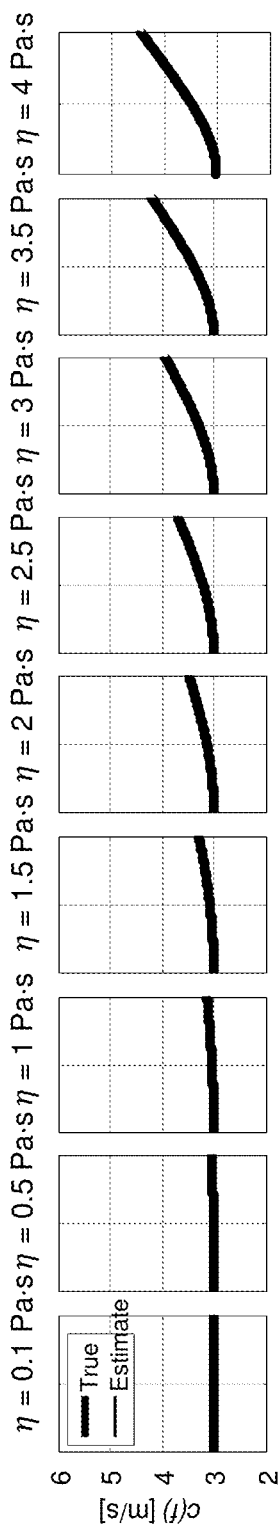
FIGS. 4A and 4B show graphs of a frequency-dependent phase velocity estimates compared to the true values for simulated particle velocity measurements in several Voigt materials (stiffness $\mu_0$=9 kPa, mass density $\rho$=1000 kg/m3, and varying viscosity $\eta_s$=[0.1–4] Pa_s), the estimates based on the proposed method, see FIG. 4A and the 2D-FT method, see FIG. 4B described by Nenadic et al. [9] are compared.
Figure 4B:
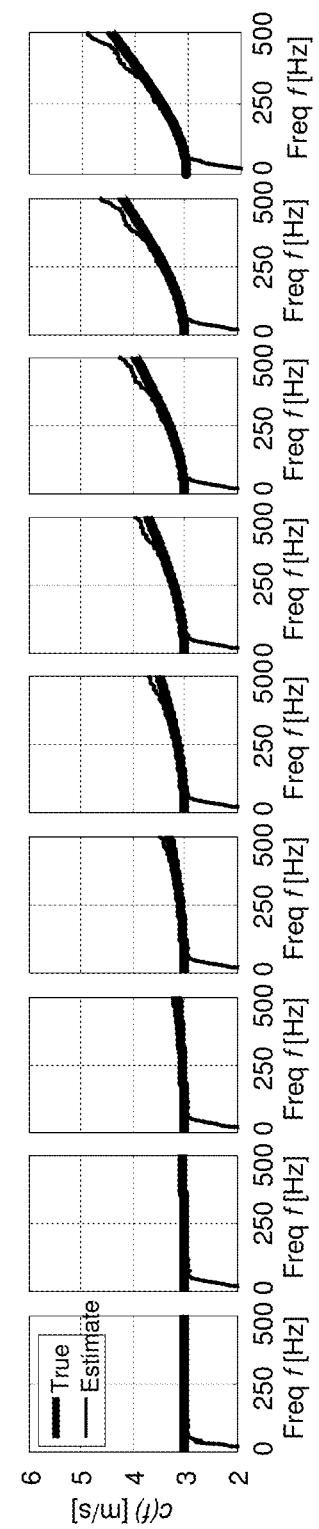

From FIG. 4A, one can notice that the estimates are very close to the true phase velocities for all or most simulations, i.e. the lines for 'True' and 'estimate' overlap in the whole range. FIG. 4B shows the results of the 2D-FT method [9] applied to the full space-time data. Here, the estimated phase velocities deviate slightly from the true values, in particular for higher frequencies and viscosity.

B. In-Vitro Results

Figure 5A:
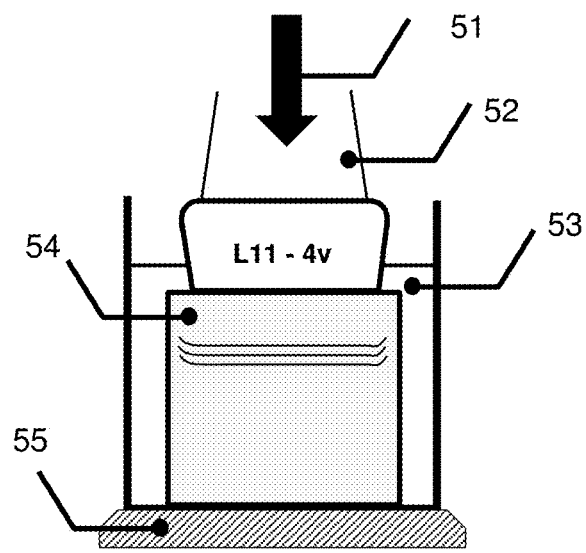
FIG. 5A schematically shows a setup of a system for ultrasound strain measurements upon application of a sudden stress.

FIG. 5A schematically shows a setup of a system for ultrasound strain measurements upon application of a sudden stress. A force 51 of e.g. 2N is applied by a L11-4v linear array ultrasound transducer 52. FIG. 5A also shows a water basin 53, a tissue 54 mimicking phantom, and a balance 55.

Figure 5B:
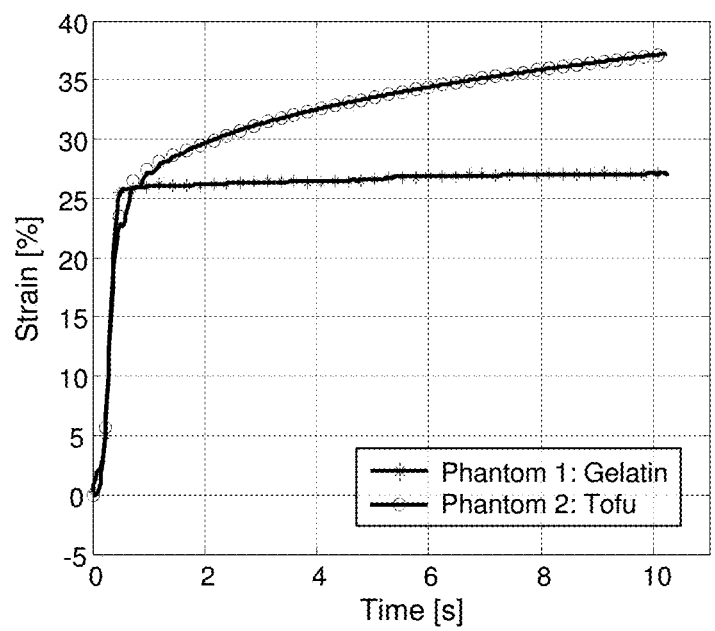
FIG. 5B shows a graph of resulting creep curves for gelatine and tofu phantoms, depicting a higher viscous creep for the latter.

FIG. 5B shows a graph of resulting creep curves for gelatine and tofu phantoms, depicting a higher viscous creep for the latter. The creep curves presented in FIG. 5B show how the gelatine and tofu phantoms display different time-strain behaviour. When subjected to a sudden stress, gelatine compresses instantly and shows little to no creep, whereas the tofu phantom creeps significantly and clearly presents more viscous behaviour.

Figure 6A:
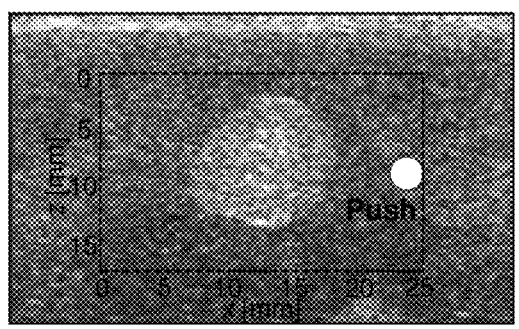
FIGS. 6A and 6C show brightness mode images of a tofu phantom containing a cylindrical inclusion of gelatin, the push locations are also illustrated.
Figure 6A:
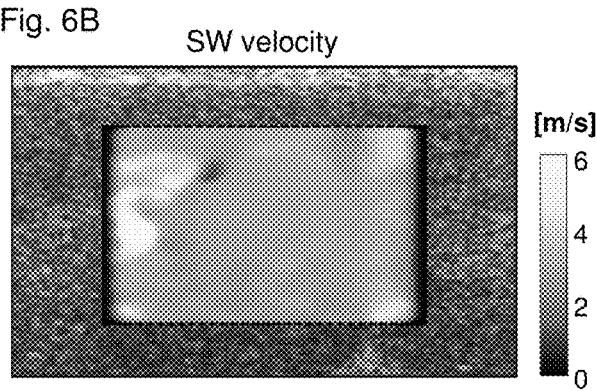
Figure 6C:
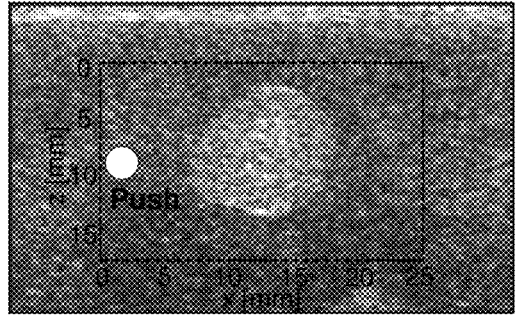
Figure 6C:
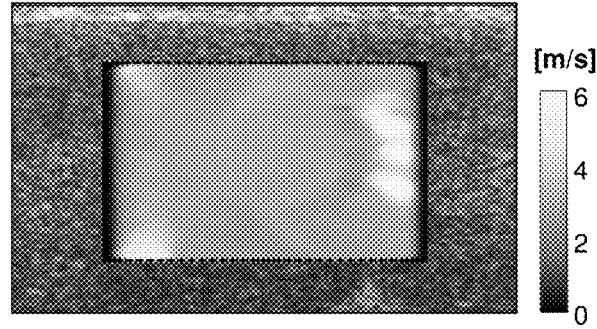
Figure 7A:
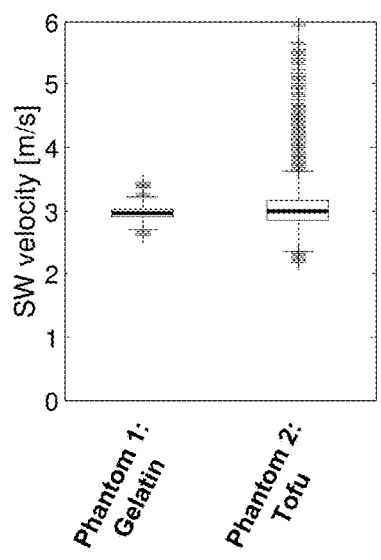
FIG. 7: Box plots displaying the distributions of shear wave velocity and viscosity in gelatine and tofu phantoms as obtained using the proposed method (FIGS. 7B and 7C) compared to velocity estimates using a cross correlation based time-of-flight method (FIG. 7A)
Figure 7B:
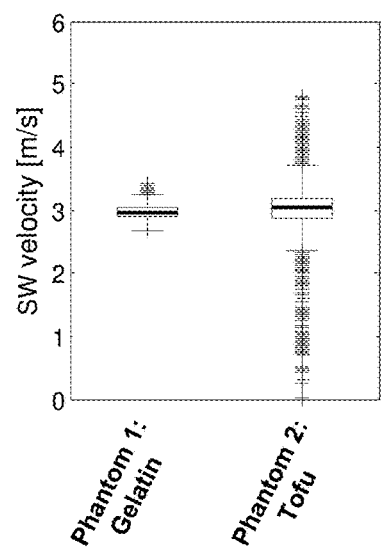
Figure 7C:
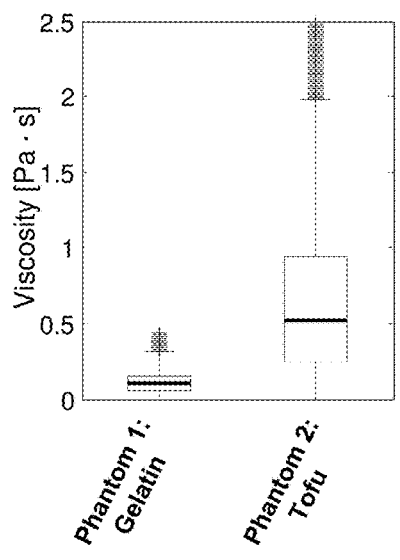

FIG. 7 summarizes the obtained pixel-based SW velocity and viscosity distributions for both phantoms when applying the proposed method. The SW velocity estimates are compared to those measured using the cross-correlation approach. In line with the mechanical characterization, the estimated viscosity is significantly higher in tofu than in gelatine, while the velocity (and therefore stiffness) is not significantly different. The spread and range of estimated values is higher in the tofu phantom as compared to the gelatine phantom. Finally, viscoelasticity imaging was performed on a tofu phantom containing a cylindrical inclusion of gelatine. The images were post-processed using a 2D median filter (kernel dimensions: 1 mm×3.5 mm) followed by a 2D Gaussian filter (standard deviation: 0.2 mm×0.6 mm). From FIG. 6, one can appreciate that the less-viscous gelatine inclusion is indeed revealed by the viscosity maps, whereas the velocity images (portraying the purely elastic behaviour) fail to expose it. Where the results obtained with a push-focus on either side of the imaging domain (FIGS. 6A and 6B) qualitatively show great similarity in the central zone of the image, one can also observe that the estimates very close the push location and at the far end do not share this degree of consistency.

Figure 8:
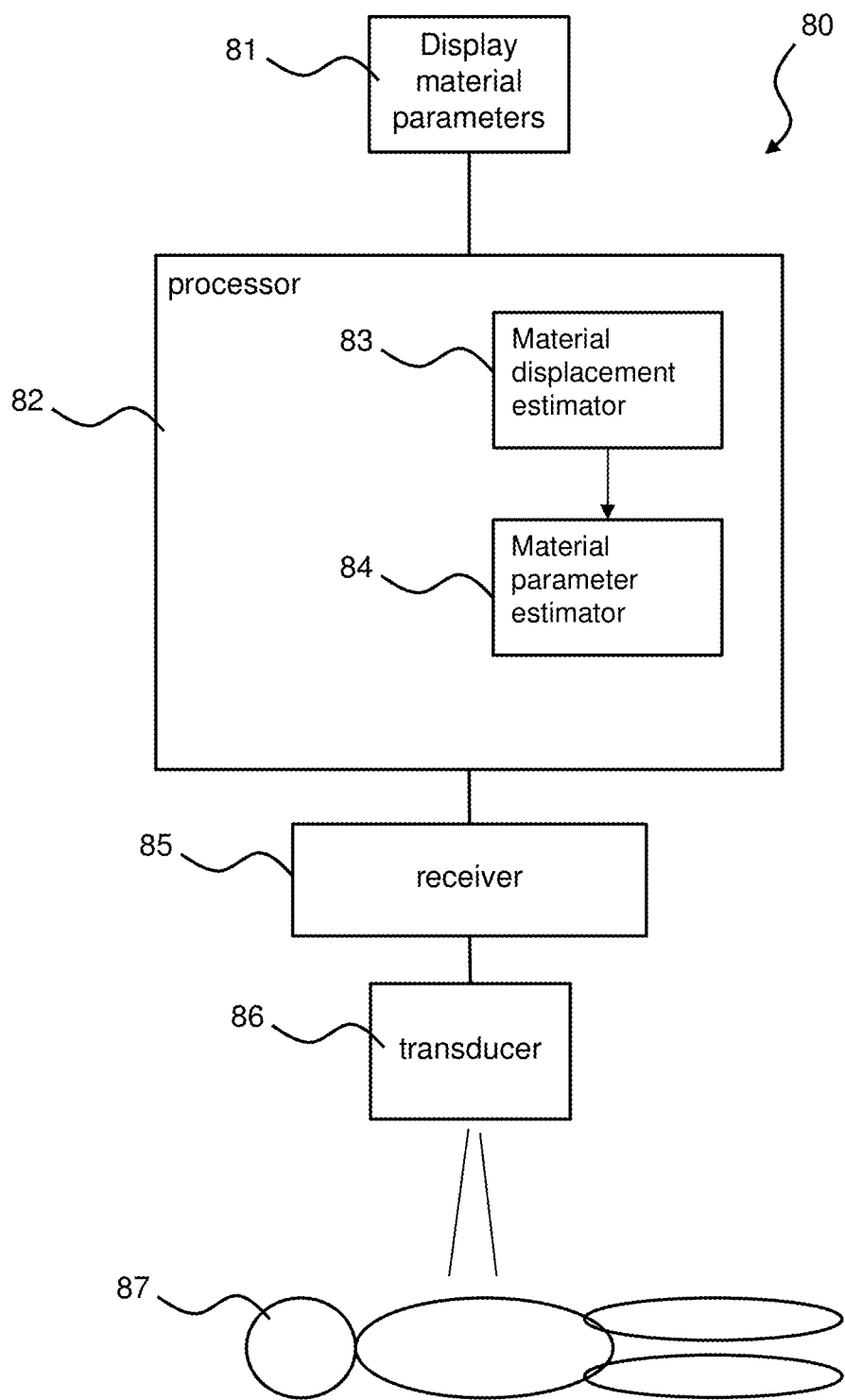
FIG. 8 schematically shown an embodiment of an estimation system.

FIG. 8 schematically shows a system 80 for estimating the viscoelasticity of a material according to an embodiment of the presently disclosed subject matter. The system 80 includes an ultrasound transducer 86 for sending ultrasound waves into the material and for measuring a plurality of time-amplitude curves, as described above. The system further includes a receiver 85 for receiving the plurality of time-amplitude curves measured at a plurality of space points. The receiver 85 may be a computer interface arranged to receive input signals and convert them to signals to be processed in a processor. The time-amplitude curves reflect time evolutions of a propagating mechanical (e.g. ultrasound) wave. The time-amplitude curves may be created by a transducer 86 arranged to send waves to a part of a body 87 and receive echoes returned by tissue in the part of the body 87.

The system 80 further includes an estimator for estimating the viscoelasticity of a material between any set of space points using the time-amplitude curves measured at those space points. The estimator may include a material displacement estimator 83, and a material parameter estimator 84. The material displacement estimator 83 is arranged to detect axial material displacements/using phase estimation methods. The material parameter estimator 84 is arranged to estimate the viscoelastic material parameters using system identification by least squares impulse response fitting. The material displacement estimator 83 and a material parameter estimator 84 may be implemented in or by a processing unit, such as a CPU 82.

In the example of FIG. 8, the system 80 further includes a display 81 for displaying 2D or 3D maps indicative of the viscoelasticity of the material. Possibly the maps are color maps indicating viscosity and elasticity parameters. An example of such a map (in grey scales) is shown in FIGS. 6E-6H. These maps can be used by a clinician to detect abnormalities in tissue, such as fatty livers.

Figure 9:
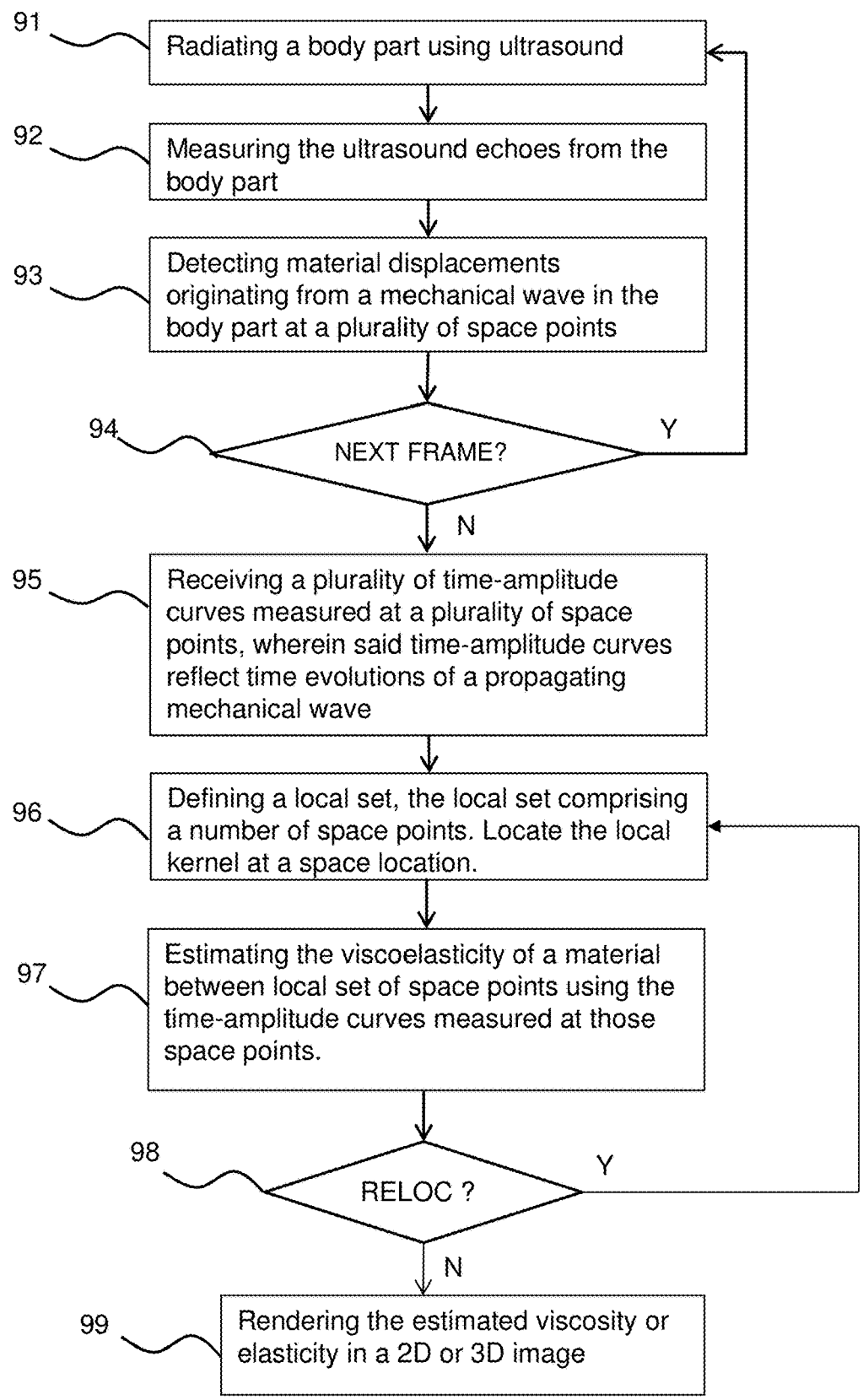
FIG. 9 shows a flow chart of an embodiment of the method.

FIG. 9 shows a flow chart of a method of estimating according to an embodiment of the presently disclosed subject matter. In step 94 it is tested if another time frame is needed to capture the full mechanical wave. In step 98 it is tested if relocation of the local kernel is needed. In case no relocation is needed to cover the region-of-interest, the viscosity or elasticity parameters can be rendered in parametric maps.

V. Conclusions and Discussion

In this work, a new approach to determine tissue viscoelasticity based on SW elastography is presented. By locally characterizing SW propagation using a system identification approach, the proposed method enables mapping of not only tissue elasticity, but also of viscosity. The developed technique extends beyond the typical time-of-flight based methods by estimating the kinetics between laterally sampled time-displacement curves instead of just their time-delay. The developed algorithm was first tested on simulated datasets, validating its technical correctness with respect to a well-defined ground truth. As observed by others, the assumption of negligible viscosity in a viscoelastic material led to inadequate estimation of SW velocity based on time-of-flight. On the contrary, by jointly estimating SW velocity and material viscosity, the proposed method appropriately assessed both aspects (FIG. 2). The impact of viscosity on time-of-flight SW velocity estimates was further investigated on a range of simulations with viscous materials ($\eta_s$=0.1 Pa s to $\eta_s$=4 Pa s). As expected, the presence of viscosity impairs the time-of-flight estimates, yielding high standard deviations along the lateral position. The proposed method suffered far less from this effect by adequately modelling the effects of viscosity on SW propagation.

On the same range of viscous materials, the resultant phase velocities derived from the estimated material properties matched the true values very well (FIG. 4). Interestingly, we observed that the 2D-FT method for phase velocity dispersion characterization displayed a bias, in particular for higher frequencies (towards 500 Hz) and viscosities. Such a bias was also noted by Rouze et al. in [12]. In this regard, we would like to point out that the simulated range of covers a realistic scope of expected viscosities in tissue. In [17], Wang and Insana investigated the viscoelastic properties of fibroadenomas and carcinomas in rats by extracting and characterizing shear-velocity dispersion curves. Based on a Kelvin-Voigt model, they reported viscosity values that range from $\eta$=0.56–3.54 Pa s On the in-vitro SW data we found that the method yielded material-property estimates which confirmed the observations made based on the mechanical material characterization; the tofu and gelatine materials have a similar stiffness, yet very distinct viscosity. As noted in Section IV-B, the spread and range of estimated values was found higher in the tofu phantom as compared to the gelatine phantom. This may originate from substantial material heterogeneity in tofu, which is less evident in gelatine. Moreover, the degraded signal-to-noise level in tofu that is caused by higher shear attenuation may have impacted the estimation accuracy and thereby its variance.

By imaging a gelatine phantom with a cylindrical tofu inclusion, we showed that the method is able to generate a viscosity map that reveals the inclusion. The eventual possibility of yielding such a viscosity map using ultrasonic SW elastography was discussed in [11], where Bercoff et al. contemplated that adding viscosity maps in SW imaging could be of great interest for tumor characterization.

The artefacts in the viscosity maps that appear close to the acoustic push focus (Sec. IV-B) occur when estimating the model parameters from data in the SW near-field. We speculate that these artifacts originate from:
1) Non-plane wave propagation in the near-field; a condition for which our 1D model does not hold.
2) The fact that the push-pulse is not a delta-Dirac in space, leading to the presence of an additional apparent "source" between the two lateral positions from which the impulse response is assessed. This violates the assumption that those two points only record a passing SW and all or most measured axial displacement originates from this propagating wave.

At the far end we also observe the presence of estimation artifacts. Here, wave aberration and low signal-to-noise ratio are likely degrading the estimates. The aforementioned artifacts can be mitigated by combining the estimates from several SW measurements obtained using different lateral push foci; herein just using those segments that yield reliable estimates. Reliability can be assessed based on location (e.g. close to the push-focus) and signal quality. Such a multi-focus strategy can also be pursued in the axial direction to cover a wide spatial range.

Compared to other methods that aim at assessing viscosity from SW measurements, we would like to stress that the proposed method is able to generate estimates in a pixel-based point-to-point fashion. This approach enables the generation of SW maps with a lateral resolution that is primordially determined by the adopted spacing between these points (in this work \2Δx). Choosing a suitable Δx amounts to a trade-off.

Decreasing Δx leads to fine estimates, close to the lateral resolution of the US acquisition. Yet, increasing Δx results in a more pronounced effect of the local material properties on the kinetics between the two points, accommodating a more robust estimation procedure in the presence of noise.

The appropriate value depends on the application; for tumor localization a resolution in the order of millimetres may be required [18], whereas characterization of diffuse hepatic steatosis may permit assessment on larger scale [19]. To be able to confirm the practical utility the prosed method, it should be tested extensively on real tissue. Such tests can initially be conducted ex-vivo, but should eventually lead to in-vivo experiments. In these conditions, the impact of noise, diffraction, aberration, along with other disturbances should be carefully investigated. Whereas the method in presented in this work was applied to SW data obtained from a single push pulse, one can imagine that the high in-vivo demands may require strategies such as supersonic SW generation and SW compounding [3]. The former produces an intense source by generating shear waves that interfere constructively along a Mach cone to boost the signal-to-noise ratio. The latter combines the results from multiple shear waves to improve reliability of the estimates. The proposed method can be straightforwardly applied in such a fashion.

Besides ameliorating the method reliability using a high quality SW dataset, we can also resort to more advanced system identification techniques based on maximum-likelihood estimators that take full advantage of the expected noise statistics to yield robust parameter estimates. Such approaches may require a careful design of the noise model for SW displacement signals, taking into account the full acquisition chain from the push source to the (Loupass) displacement estimator and any subsequent pre-processing.

Where the results presented herein were obtained assuming a Voigt material model, the approach can be readily generalized to facilitate characterization in terms of other viscoelastic material models, such as the typically adopted Maxwell or 3-parameter model. One would then merely need to select the appropriate frequency dependent shear modulus $\mu(\omega)$, and solve the minimization problem as described in Eqn. (10) for the corresponding material parameters. It should be noted, however, that the optimization procedure for a 3-parameter model with 2 stiffness constants is most-likely more challenging than for the 2-parameter Maxwell and Voigt models. If the proposed method's applicability is confirmed in vivo, it could in principle be readily implemented on any SW device without requiring hardware changes. A glaring application then lies in the area of tumour localization characterization, but also assessment of fatty liver disease processes such as steatosis, fibrosis and cirrhosis is of interest.

Estimation of soft tissue elasticity is of interest in several clinical applications. For instance, tumors and fibrotic lesions are notoriously stiff compared to benign tissue. A fully quantitative measure of lesion stiffness can be obtained by shear wave elastography, a method that uses an acoustic radiation force to produce laterally propagating shear waves that can be tracked to obtain the velocity, which is in turn related to the Young's modulus. However, not only elasticity, but also viscosity plays a role in the propagation process of shear waves. In fact, viscosity itself is a parameter that can be exploited for detection and characterization of malignant lesions.

In the above described embodiments, a new method was described that enables imaging viscosity from shear wave elastography by local model-based system identification. By testing the method on simulated datasets and performing in vitro experiments, it can be shown that the proposed technique is able to locally characterize the viscoelastic material properties from shear wave measurements, opening up new possibilities for noninvasive tissue characterization.

It should be noted that the above-mentioned embodiments illustrate rather than limit the presently disclosed subject matter, and that those skilled in the art will be able to design many alternative embodiments.

In the claims, any reference signs placed between parentheses shall not be construed as limiting the claim. Use of the verb "include" and its conjugations does not exclude the presence of elements or steps other than those stated in a claim. The article "a" or "an" preceding an element does not exclude the presence of a plurality of such elements. The presently disclosed subject matter may be implemented by hardware including several distinct elements, and by a suitably programmed computer. In the device claim enumerating several methodologies, several of these methodologies may be embodied by one and the same item of hardware. The mere fact that certain measures are recited in mutually different dependent claims does not indicate that a combination of these measures cannot be used to advantage.

REFERENCES

[1] Kenneth Hoyt, Benjamin Castaneda, Man Zhang, Priya Nigwekar, P Anthony di Sant'Agnese, Jean V Joseph, John Strang, Deborah J Rubens, and Kevin J Parker. Tissue elasticity properties as biomarkers for prostate cancer. Cancer Biomarkers, 4(4-5):213-225, 2008.

[2] Kathryn Nightingale, Stephen McAleavey, and Gregg Trahey. Shearwave generation using acoustic radiation force: in vivo and ex vivo results. Ultrasound in medicine & biology, 29(12):1715-1723, 2003.

[3] Jérémy Bercoff, Mickael Tanter, and Mathias Fink. Supersonic shear imaging: a new technique for soft tissue elasticity mapping. IEEE transactions on ultrasonics, ferroelectrics, and frequency control, 51(4):396-409, 2004.

[4] Mark L Palmeri, Michael H Wang, Jeremy J Dahl, Kristin D Frinkley, and Kathryn R Nightingale. Quantifying hepatic shear modulus in vivo using acoustic radiation force. Ultrasound in medicine & biology, 34(4):546-558, 2008.

[5] Michael H Wang, Mark L Palmeri, Cynthia D Guy, Liu Yang, Laurence W Hedlund, Anna Mae Diehl, and Kathryn R Nightingale. In vivo quantification of liver stiffness in a rat model of hepatic fibrosis with acoustic radiation force. Ultrasound in medicine & biology, 35(10):1709-1721, 2009.

[6] Michael H Wang, Mark L Palmeri, Veronica M Rotemberg, Ned C Rouze, and Kathryn R Nightingale. Improving the robustness of time-of-flight based shear wave speed reconstruction methods using ransac in human liver in vivo. Ultrasound in medicine & biology, 36(5):802-813, 2010.

[7] Ned C Rouze, Michael H Wang, Mark L Palmeri, and Kathryn R Nightingale. Robust estimation of time-of-flight shear wave speed using a radon sum transformation. IEEE transactions on ultrasonics, ferroelectrics, and frequency control, 57(12), 2010.

[8] Joyce McLaughlin and Daniel Renzi. Shear wave speed recovery in transient elastography and supersonic imaging using propagating fronts. Inverse Problems, 22(2):681, 2006.

[9] Ivan Nenadic, Matthew W Urban, Bo Qiang, Shigao Chen, and James Greenleaf. Model-free quantification of shear wave velocity and attenuation in tissues and its in vivo application. The Journal of the Acoustical Society of America, 134(5):4011-4011, 2013.

[10] Thanasis Loupas, J T Powers, and Robert W Gill. An axial velocity estimator for ultrasound blood flow imaging, based on a full evaluation of the Doppler equation by a two-dimensional autocorrelation approach. IEEE transactions on ultrasonics, ferroelectrics, and frequency control, 42(4):672-688, 1995.

[11] Jérémy Bercoff, Mickaël Tanter, Marie Muller, and Mathias Fink. The role of viscosity in the impulse diffraction field of elastic waves induced by the acoustic radiation force. IEEE transactions on ultrasonics, ferroelectrics, and frequency control, 51(11):1523-1536, 2004.

[12] Ned C Rouze, Mark L Palmeri, and Kathryn R Nightingale. An analytic, Fourier domain description of shear wave propagation in a viscoelastic medium using asymmetric Gaussian sources. The Journal of the Acoustical Society of America, 138(2):1012-1022, 2015.

[13] Raffaella Righetti, Mariapaola Righetti, Jonathan Ophir, and Thomas A Krouskop. The feasibility of estimating and imaging the mechanical behavior of poroelastic materials using axial strain elastography. Physics in medicine and biology, 52(11):3241, 2007.

[14] Mallika Sridhar and Michael F Insana. Ultrasonic measurements of breast viscoelasticity. Medical physics, 34(12):4757-4767, 2007.

[15] Michael F Insana, Claire Pellot-Barakat, Mallika Sridhar, and Karen K Lindfors. Viscoelastic imaging of breast tumor microenvironment with ultrasound. Journal of mammary gland biology and neoplasia, 9(4):393-404, 2004.

[16] Rudolph Emil Kalman et al. A new approach to linear filtering and prediction problems. Journal of basic Engineering, 82(1):35-45, 1960.

[17] Yue Wang and Michael F Insana. Viscoelastic properties of rodent mammary tumors using ultrasonic shear-wave imaging. Ultrasonic imaging, 35(2):126-145, 2013.

[18] Thomas A Stamey, Fuad S Freiha, John E McNeal, Elise A Redwine, Alice S Whittemore, and Hans-Peter Schmid. Localized prostate cancer, relationship of tumor volume to clinical significance for treatment of prostate cancer. Cancer, 71(S3):933-938, 1993.

[19] Thomas Deffieux, Jean-Luc Gennisson, Laurence Bousquet, Marion Corouge, Simona Cosconea, Dalila Amroun, Simona Tripon, Benoit Terris, Vincent Mallet, Philippe Sogni, et al. Investigating liver stiffness and viscosity for fibrosis, steatosis and activity staging using shear wave elastography. Journal of hepatology, 62(2):317-324, 2015.

The invention claimed is:

1. A method of estimating viscoelasticity of a material using ultrasound, the method comprising:
   receiving a plurality of time-amplitude curves measured at a plurality of space points,
   wherein the time-amplitude curves reflect time evolutions of a propagating mechanical wave, the propagating mechanical wave being a shear wave generated by application of ultrasound; and
   estimating the viscoelasticity of the material between any set of space points using the time-amplitude curves measured at the set of space points,
   wherein the step of estimating the viscoelasticity comprises:
      determining a model to describe the response of the material between said space points to a mechanical wave, and
      obtaining model parameters of the model using system identification, wherein the system identification is based on maximum likelihood or least-squares impulse response fitting; and
   estimating an impulse response for the system identification by:
      defining a time-amplitude curve measured at a space point as an input time-amplitude curve;
      defining a time-amplitude curve measured at another space point as an output time-amplitude curve;
      defining the impulse response that describes the relation between the input time-amplitude curve and the output time-amplitude curve; and
      estimating the impulse response from the input time-amplitude curve and the output time-amplitude curve.

2. The method according to claim 1, wherein estimating the impulse response is performed using a parametric model, the parametric model comprising one of:
   a two-point Green's function of a Navier-Stokes equation for a viscoelastic material model, describing mechanical wave propagation from one point to another; and
   a convection-diffusion model.

3. The method according to claim 1 further comprising generating a 2D or 3D map of viscosity or elasticity, wherein generating a map of viscosity or elasticity includes:
   iteratively performing the following steps until the region of interest has been covered:
      defining a local set, the local set having a number of space points;
      placing a local kernel at a space location; the space location corresponding to the local set, the space location being within the region of interest; and
      repeating the step of estimating the viscoelasticity of the material at the space location and moving the local kernel to a next space location within the region of interest; and
   rendering an estimated viscosity or elasticity in a 2D or 3D image.

4. The method according to claim 1 further comprising generating a 2D or 3D tensor map, wherein generating a tensor includes:
   mapping the plurality of estimated model parameters between the space points to a tensor;
   wherein the mapping is obtained by solving a set of equations that describes a relation between the model parameters, the space points, and the tensor.

5. The method according to claim 4, wherein the tensor is a vector that describes local mechanical wave propagation direction and velocity magnitude.

6. The method according to claim 5, further comprising rendering the vector map in a 2D or 3D image.

7. The method according to claim 4, further comprising visualizing the tensor map in a 2D or 3D image.

8. A method of detecting abnormalities in living tissue, the method comprising:
   radiating at least part of the living tissue using ultrasound waves;
   detecting echoes of the ultrasound waves; and
   estimating the viscoelasticity of the living tissue using the method according to claim 1.

9. A system for estimating viscoelasticity of a material using ultrasound, the system comprising:
   a receiver for receiving a plurality of time-amplitude curves measured at a plurality of space points, wherein the time-amplitude curves reflect time evolutions of a propagating mechanical wave, the propagating mechanical wave being a shear wave generated by application of ultrasound; and
   an estimator for estimating the viscoelasticity of the material between any set of space points using the time-amplitude curves measured at those space points, the estimator being configured to estimate the viscoelasticity of the material by:
      determining a model to describe the response of the material between said space points to a mechanical wave, and
      obtaining the model parameters of the model using system identification, wherein the system identification is based on maximum likelihood or least squares impulse response fitting; and
   wherein the estimator is configured to estimate an impulse response for the system identification by:
      defining a time-amplitude curve measured at a space point as an input time-amplitude curve;
      defining a time-amplitude curve measured at another space point as an output time-amplitude curve;
      defining the impulse response that describes the relation between the input time-amplitude curve and the output time-amplitude curve; and
      estimating the impulse response from the input time-amplitude curve and the output time-amplitude curve.

10. The system according to claim 9 further comprising an ultrasound transducer for sending ultrasound waves into the material and for measuring the plurality of time-amplitude curves.

11. The system according to claim 9 further comprising a display for displaying 2D or 3D maps indicative of the viscoelasticity of the material.

* * * * *